(12) United States Patent
Hug et al.

(10) Patent No.: US 6,358,522 B1
(45) Date of Patent: Mar. 19, 2002

(54) PHARMACEUTICAL COMPOSITIONS CONTAINING LIPASE INHIBITOR

(75) Inventors: Manuela Hug, Weil am Rhein (DE); Hans-Peter Märki, Basel; Marcel Meier, Pratteln, both of (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/370,846

(22) Filed: Aug. 10, 1999

(30) Foreign Application Priority Data

Aug. 14, 1998 (EP) ............................................. 98115311
May 12, 1999 (EP) ............................................. 99109516

(51) Int. Cl.⁷ .............................. A61K 9/28; A61K 9/68
(52) U.S. Cl. ........................ 424/441; 424/464; 424/400; 514/57
(58) Field of Search .................................. 424/400, 405, 424/408, 410, 439, 441, 464, 465, 474; 252/380; 514/23, 54, 57

(56) References Cited

U.S. PATENT DOCUMENTS

| | | |
|---|---|---|
| 4,005,195 A | 1/1977 | Jandacek |
| 4,598,089 A | 7/1986 | Hadvary et al. |
| 5,447,953 A | 9/1995 | Isler et al. |
| 5,643,874 A | * 7/1997 | Bremer et al. ................ 514/12 |

FOREIGN PATENT DOCUMENTS

| | | |
|---|---|---|
| EP | 0 638 317 | 2/1995 |
| WO | WO 92/17077 | 10/1992 |
| WO | WO 98/34607 | 8/1998 |

OTHER PUBLICATIONS

Chemical Abstract No. XP–002123841, vol. 127, No. 20 (1997).
Chemical Abstract No. XP–002123842, vol. 128, No. 24 (1998).
Sjostrom, et al., Randomised placebo–controlled trial of orlistat for weight loss and prevention of weight regain in obese patients, The Lancet, vol. 352, No. 9123, pp. 167–172 (1998)

* cited by examiner

*Primary Examiner*—Dameron L. Jones
(74) *Attorney, Agent, or Firm*—George W. Johnston; John P. Parise

(57) ABSTRACT

The present invention provides orally administrable pharmaceutical compositions containing an inhibitor of gastrointestinal lipase, one (or more) additive(s) of the group consisting of substantially non-digestible, substantially non-fermentable, hydrophilic and/or hydrocolloidal food grade thickeners and emulsifiers, and auxiliary excipients. Methods are provided for preventing and treating anal leakage of oil in a patient by administering the compositions of the present invention to the patient.

14 Claims, No Drawings

PHARMACEUTICAL COMPOSITIONS CONTAINING LIPASE INHIBITOR

BACKGROUND OF THE INVENTION

The present invention relates to pharmaceutical compositions containing an inhibitor of gastrointestinal lipases, one (or more) additive(s) of the group consisting of substantially non-digestible, substantially non-fermentable, hydrophilic and/or hydrocolloidal food grade thickeners and emulsifiers, and excipients.

An example of an inhibitor of gastrointestinal lipases is orlistat, previously known as tetrahydrolipstatin or THL. Orlistat reduces the absorption of dietary fat. Its use for the control or prevention of obesity and hyperlipidaemia is described in U.S. Pat. No. 4,598,089. Orlistat is the N-formyl-L-leucine ester with (3S,4S)-3-hexyl-4-[(2S)-2-hydroxy-tridecyl]-2-oxetanone.

Anal leakage of oil (oily spotting) is an adverse effect which is occasionally observed in patients treated with lipase inhibitors. This phenomenon reflects physical separation of some liquid unabsorbed dietary fat from the bulk of unabsorbable solids in the lower large intestine. This physical separation and thus anal leakage of oil can be prevented with the pharmaceutical compositions of the present invention.

In the U.S. Pat. No. 5,447,953 it has been demonstrated that by combining a lipase inhibitor with substantial amounts of water-insoluble crude fibers, the inhibiting effect on fat absorption can be increased. This synergistic effect is likely attributable to acceleration of gastrointestinal transit of food by the water-insoluble fiber component. The consequent shortening of the time period available for fat digestion combined with the reducing effect on lipase activity intensifies the inhibitory effect on fat absorption.

SUMMARY OF THE INVENTION

Surprisingly, it has now been found that the separation of unabsorbed oil from the feces and thus anal oil leakage can be reduced or prevented, when a lipase inhibitor such as orlistat is administered in combination with low amounts of one or more substantially non-digestible, substantially non-fermentable, hydrophilic and/or hydrocolloidal food grade thickeners and/or emulsifiers.

It is an object of the present invention to use substantially non-digestible, substantially non-fermentable hydrophilic and/or hydrocolloidal food grade thickeners and/or emulsifiers for the combined simultaneous, separate or chronologically spaced administration with lipase inhibitors, e.g. orlistat, in the treatment of obesity and hyperlipaemia.

It is another object of the present invention to provide pharmaceutical compositions containing substantially non-digestible, substantially non-fermentable hydrophilic and/or hydrocolloidal food grade thickeners and/or emulsifiers and lipase inhibitor for administration to a patient in unit dosage form to prevent anal oil leakage.

The invention is further concerned with the use of the above thickeners and/or emulsifiers for treating or preventing the syndrome of anal leakage of oil occurring after the administration of a lipase inhibitor, such as orlistat, or after ingestion of food containing poorly absorbable or non-absorbable fats or oils or undigestible oily fat substitutes. Methods for preventing anal oil leakage in patients comprising administering to the patients compositions containing a lipase inhibitor and thickeners and/or emulsifiers are described herein.

DETAILED DESCRIPTION OF THE INVENTION

In accordance with the present invention, substantially non-digestible, substantially non-fermentable hydrophilic and/or hydrocolloidal food grade thickeners and/or emulsifiers are administered with lipase inhibitors, e.g. orlistat, to treat or prevent anal oil leakage. The substantially non-digestible, substantially non-fermentable hydrophilic and/or hydrocolloidal food grade thickeners and/or emulsifiers can be administered with the lipase inhibitor either simultaneously or sequentially. The present invention provides pharmaceutical compositions containing lipase inhibitor and substantially non-digestible, substantially non-fermentable hydrophilic and/or hydrocolloidal food grade thickeners and/or emulsifiers for administration to patients in unit dosage form to treat or prevent anal oil leakage. The compositions of the present invention also preferably contain auxiliary excipients such as binders, diluents, and lubricants. A preferred lipase inhibitor is orlistat. Orlistat is the N-formyl-L-leucine ester with (3S,4S)-3-hexyl-4-[(2S)-2-hydroxy-tridecyl]-2-oxetanone. Further examples of lipase inhibitors which can be used in the scope of the present invention are lipstatin, panclicins, hesperidin, ebelactones, esterastin and their derivatives, and valilactone.

In accordance with the present invention, the term "food grade"thickener or emulsifier is any conventional thickener or emulsifier used in foods.

Preferred thickeners for use with the present invention are water soluble natural, synthetic or semisynthetic polysaccharides, such as methylcellulose, xanthan gum, psyllium seed, ispaghula husk, plantago ovata seeds, karaya gum and mixtures of such compounds.

Methyl cellulose is the methyl ether of cellulose. It is slowly soluble in water, giving a viscous, colloid solution.

Xanthan gum is a biosynthetic hydrocolloidal high molecular weight exopolysaccharide produced by pure culture fermentation of Xanthomonas campestris. It contains D-glucose, D-mannose, and D-glucuronic acid as the dominant hexose units and is manufactured as the sodium, potassium, or calcium salt.

Psyllium seed husk, seed coat is a source of soluble fibre. It comprises cellulose containing walls of endosperm, and mucilage containing epidermis of small dried ripe seeds. A colorless transparent mucilage forms upon contact with water.

Ispaghula husk is *psyllium* hydrophilic mucilloid. It comprises the epidermis and collapsed adjacent layer of Plantago species, e.g. *Pl. psyllium*. It swells rapidly upon contact with water to form a stiff mucilage.

Plantago ovata seeds (seed husk and seed coat) is a source of soluble fibre. It comprises cellulose containing walls of endosperm, and mucilage containing epidermis of small dried ripe seeds. A colorless transparent mucilage forms upon contact with water.

Karaya gum is a hydrocolloidal exudate or gum from Sterculia species. It forms a homogenous adhesive gelatinous mass upon contact with water.

Examples of these types of thickeners are contained in over-the-counter (OTC) products and/or food additives, such as:

METHOCEL A4M, a trademark of Dow Chemical Co. for a high viscosity methyl cellulose, KELTROL TF, a trademark of Merck & Co. Inc., Rahway N.J., for xanthan gum, MUCILAR; psyllium seed (*Psyllii seminis testa*), a product of Spirig AG, CH-4622 Egerkingen, METAMUCIL, ispaghula husk (*Ispaghulae testae pulvis*) a product of Procter & Gamble, CH-1211 Geneve 2, AGIOCUR, plantago ovata seeds, a product of Madaus AG, D-5000 Köln 91, NORMACOL MITE, a trademark of Norgine Ltd., Great Britain, for karaya gum, POLY-KARAYA, a trademark of Delalande for karaya gum of Interdelta SA, CH-1701 Fribourg.

A further example of a thickener is FIBERCON (polycarbophil), a trademark of Lederle Laboratories Division, American Cyanamid Co., Pearl River N.Y., for the calcium salt of a synthetic loosely crosslinked hydrophilic resin of the polycarboxylate type.

As emulsifiers which can be utilized in the compositions of the invention, there can be cited saccharose polyesters, such as Ryoto Sugar Esters, e.g. Ryoto Sugar Ester S-170. Ryoto Sugar Esters are a trade name of Mitsubishi-Kasi Foods Corp., Chuo-Ku, Tokyo 104, for sucrose fatty acid esters. Ryoto Sugar Ester S-170 contains sucrose stearic acid polyesters.

Examples of excipients which can be used in the pharmaceutical compositions of the invention are binders, diluents and lubricants, such as AVICEL, polyvinyl pyrrolidone (povidone), talc, stearic acid and sodium stearyl fumarate; sweeteners, such as sorbitol, glucose, saccharose, saccharine-sodium salt and sodium cyclamate; flavour agents, such as passion fruit, citron and limette; flavour enhancers, such as citric acid, monosodium citrate, sodium chloride and chinine sulfate; effervescing agents, such as sodium bicarbonate and tartaric acid; disintegrants, such as sodium starch glycolate; antimicrobial agents, such as p-hydroxybenzoic acid methyl or propyl ester; detergents, such as sodium lauryl sulfate, and colouring agents, such as β-carotene.

AVICEL essentially comprises microcrystalline cellulose. It is available from FMC Corporation, Pharmaceutical Division, 1735 Market Street, Philadelphia, Pa. 19103, e.g. as AVICEL RC-591 or CL-611, which are mixtures of microcrystalline cellulose (about 92%) and carboxymethyl-cellulose sodium (about 8%), AVICEL PH 101 or PH 105, which is microcrystalline cellulose with an average particle size of 50 or 20 $\mu$, respectively; and AVICEL CE-15 a mixture of microcrystalline cellulose and guar gum.

As indicated above, anal leakage of oil, occasionally observed with the therapeutic use of lipase inhibitors such as orlistat, can be reduced or prevented with the pharmaceutical compositions of the invention. This is illustrated by the following in vivo experiments:

Rats maintained on high fat diet were used as models. Inhibition of fat absorption by diet-admixed orlistat provoked anal leakage of liquid oil. However, the amount of oil leakage could not easily be determined. Due to coprophagia and extensive grooming activity the rats distributed the oil to a large extent over their fur. Moreover, this stressful condition of unsuccessful grooming provoked considerable excitation of the animals. The area of greasy fur increased in proportion to the amount of unabsorbed fat and was reduced by dietary admixture of selected examples of the above defined food additives. However, for reasons of animal care for comparative evaluation of the additives a surrogate parameter was used to assess effects on oil leakage. Following a meal containing orlistat, unabsorbed fat is temporarily stored in the caecum of the rat prior to excretion. The fat is partly present as floating liquid oil, partly associated with unabsorbable solids. In validation studies it could be demonstrated that the effect of food additives to bind and sequester unabsorbed liquid oil in the solid phase of the caecum is a reliable surrogate parameter predictive for a corresponding reduction of subsequent oil leakage.

The high fat basal diet used contained by weight 56% lab chow, 12% glucose and 32% olive oil. Food additives were supplemented at three levels, accounting for 12.4, 4.5 and 1.2% of the composite diet by weight. Control diets were supplemented with a corresponding amount of starch. All diets were moistened with water to a similar consistency to facilitate acceptability by the animals. Groups of 6–7 female rats (body weight: 120–140 g) were allocated to each diet. After dietary adaptation for one week, the rats were fasted for 24 hours and on the subsequent experimental day the diets were supplied as single meal (basal diet: 4.25 g, additives or starch: 0.6, 0.2 and 0.05 g). In order to completely block absorption of oil and thus produce a defined amount of unabsorbed fat a high dose of orlistat (45 mg) was dissolved in the olive oil fraction (1.5 ml) of the meal. The animals were sacrificed three hours after supplying the meal. At this point in time the caecum contained the largest fraction of administered dietary oil. To determine the relative amounts of bound and free oil in the caecum, the caecal contents were centrifuged(2000 g, 30 min) and the lipid content of the oil/water and solid phase was quantitated gravimetrically following extraction with solvent.

The food additives tested in the first experimental series were methylcellulose (MC), Ryoto sugar ester S-170 (RS) and xanthan gum (XG). The fat content of the liquid and solid phases in the caecum was expressed as percentage of the amount of oil supplied with the meal. Mean values for experimental groups fed the additives, as compared to controls (where the thickening or emulsifying additive was replaced by the corresponding weight of starch(ST)), are shown in the following table. For statistical assessment of the effect of the additives, Student's t-test was used: n.s.= $p>0.05$, *=$p<0.05$, =$p<0.01$, *=$p<0.001$.

Fat content in caecum in % of the amount of oil supplied:

| additive   | oil phase   | solid phase |
|------------|-------------|-------------|
| MC 0.05 g  | 24.8 n.s.   | 16.8 *      |
| ST 0.05 g  | 25.4        | 13.4        |
| MC 0.20 g  | 17.0 **     | 29.2 ***    |
| ST 0.20 g  | 24.6        | 13.2        |
| MC 0.60 g  | 5.0 ***     | 32.9 ***    |
| ST 0.60 g  | 37.9        | 9.6         |
| RS 0.05 g  | 18.3 n.s.   | 13.6 *      |
| ST 0.05 g  | 23.6        | 9.0         |
| RS 0.20 g  | 22.4 n.s.   | 23.3 ***    |
| ST 0.20 g  | 24.2        | 11.0        |
| RS 0.60 g  | 3.1 ***     | 37.1 ***    |
| ST 0.60 g  | 15.8        | 11.9        |
| XG 0.05 g  | 12.7 ***    | 20.3 ***    |
| ST 0.05 g  | 23.6        | 9.0         |
| XG 0.20 g  | 1.1 ***     | 23.2 ***    |
| ST 0.20 g  | 24.2        | 11.0        |
| XG 0.60 g  | 0.7 ***     | 18.9 ***    |
| ST 0.60 g  | 23.6        | 10.9        |

As mentioned above 0.6, 0.2 and 0.05 g of food additive provided with the test meal correspond to 12.4, 4.5 and 1.2% by weight in the water-free composite diet.

The results shown above clearly demonstrate that in animals administered orlistat in combination with an additive according to the invention, the fraction of unabsorbed fat sequestered in the solid phase of the caecum was significantly increased (and liquid oil reduced) in comparison to control animals supplied with a corresponding amount of starch. Accordingly, the additives are effective in reducing or preventing anal leakage of liquid oil.

Using the same experimental procedure several OTC products containing additives according to the invention as well as water-insoluble crude fiber products were evaluated in a second experimental series. To ensure a relevant comparison of the products their variable content of active additive or fiber was taken into account. Accordingly, the amount of each product added to the diet was chosen in such a way that all the test meals contained the same amount of active additive or fiber (0.2 g, 4.5% by weight). The results of these experiments are given in the following table:

Fat content in caecum in % of the amount of oil supplied:

| OTC product | solid phase | |
|---|---|---|
| AGIOCUR 0.30 g | 20 | *** |
| FIBERCON 0.35 g | 18 | *** |
| Starch Control 0.20 g | 12 | |
| NORMACOL MITE 0.32 g | 19 | ** |
| METAMUCIL 0.41 g | 17 | ** |
| Starch Control 0.20 g | 13 | |
| POLY-KARAYA 0.50 g | 20 | *** |
| Wheat bran 0.42 g | 15 | n.s. |
| Oat bran 1.60 g | 11 | n.s. |
| Starch Control 0.20 g | 12 | |

As mentioned above, the weight of OTC products indicated in the table correspond to 0.2 g active thickening or emulsifying additive or water-insoluble fiber.

The data demonstrate binding and sequestering of caecal oil and thus efficacy in preventing anal leakage of oil for the OTC compounds AGIOCUR, FIBERCON, METAMUCIL, NORMACOL MITE and POLY-KARAYA. Moreover, the results show as well the superiority of additives according to the invention, as exemplified by POLY-KARAYA, over crude water-insoluble fibers, such as oat and wheat bran (no significant effect), which have been proposed in U.S. Pat. No. 5,447,953 to improve the inhibitory effect on fat absorption.

The compositions of the invention conveniently contain 1 to 300, preferably from 3 to 30 parts by weight of an emulsifier or thickener for 1 part by weight of orlistat or another lipase inhibitor. They conveniently further contain from 1 to 500, preferably from 3 to 200 parts by weight of auxiliary excipients for 1 part by weight of the lipase inhibitor.

The compositions of the invention can be in the form of tablets, capsules or liquid formulations, that may be reconstituted from powder, granules, pellets, standard or effervescent tablets. They can also be formulated as chewable tablets or lozenges. Furthermore, the compositions can also be incorporated into food preparations, such as wafers, crackers or biscuits.

The composition of the invention can also be in the form of a commercial pack containing a lipase inhibitor, such as orlistat, and one or more of the above mentioned thickeners and emulsifiers, with instructions for its use for the simultaneous, separate or chronologically spaced use in the treatment of obesity or hyperlipidaemia.

For the treatment or prevention of obesity or hyperlipidaemia, a composition of the invention containing from 50 to 500 mg of orlistat or another lipase inhibitor and from 150 mg to 15 g of an emulsifier or thickener can be administered orally once, twice or three times per day.

A preferred composition of the invention is a tablet for the treatment of obesity, consisting essentially of orlistat as the active ingredient and of karaya gum as the thickener, wherein the dosage is from 50 to 150 mg of orlistat and from 3 to 30 parts by weight of karaya gum or xanthan gum per 1 part by weight of orlistat, most preferably wherein the dosage is about 60 mg of orlistat and about 1.5 g of karaya gum or xanthan gum. Preferably, the tablet is chewable.

A method of preventing the syndrome of anal leakage of oil in a patient, comprises orally administering to the patient from 1 to 3 chewable tablets per meal consumed by the patient, wherein each of the tablets contains from 50 to 150 mg of orlistat and from 3 to 30 parts by weight of karaya gum or xanthan gum per 1 part by weight of orlistat. Preferably, this method comprises orally administering orlistat and karaya gum or xanthan gum in a dosage amount of about 100 mg of orlistat and of about 2 g of karaya gum or xanthan gum per meal. The composition is preferably administered to a patient per fat containing main meal consumed by the patient, for example, at breakfast, lunch and dinner.

The following non-limiting examples illustrate pharmaceutical preparations that can be produced in a manner known per se:

EXAMPLE 1

| Powder for reconstitution: | |
|---|---|
| Orlistat | 0.12 g |
| Xanthan gum | 1.20 g |
| Sorbitol | 9.91 g |
| AVICEL CL 611 | 1.20 g |
| β-Carotene 1% CWS | 0.06 g |
| Citric acid | 0.10 g |
| p-Hydroxybenzoic acid methyl ester | 0.15 g |
| p-Hydroxybenzoic acid propyl ester | 0.03 g |
| Flavouring agent (passion fruit) | 0.13 g |
| AVICEL PH 105 | 4.00 g |
| Monosodium citrate | 1.00 g |
| Saccharine-sodium salt | 0.10 g |
| Total | 18.00 g |

An oral suspension can be obtained by adding tap-water to the above powder to a volume of about 50 ml.

EXAMPLE 2

| Chewable tablets: | |
|---|---|
| Orlistat | 0.060 g |
| Karaya gum | 1.500 g |
| Polyvinyl pyrrolidone | 0.750 g |
| Sorbitol | 0.970 g |
| AVICEL CE-15 | 1.000 g |
| Talc | 0.480 g |
| Stearic acid (micro-fine powder) | 0.240 g |
| Total | 5.000 g |

The indicated amounts of orlistat, karaya gum, polyvinyl pyrrolidone, sorbitol and AVICEL CE 15 are mixed and sieved. The talc and stearic acid are sieved and mixed with the above obtained mixture. The material is then compressed to chewable tablets with a diameter of 2 cm and a weight of 5 g.

EXAMPLE 3

Pelletized formulation containing an emulsifier:

1. Orlistat pellets:

| | |
|---|---|
| Finely milled orlistat | 120 mg |
| Microcrystalline cellulose | 93.6 mg |
| Sodium starch glycolate | 7.2 mg |
| Sodium lauryl sulfate | 7.2 mg |
| Povidone | 12 mg |
| Total | 240 mg |

For a batch size of 4 kg pellets the following procedure is applied:

Sodium lauryl sulfate (120 g) and povidone (200 g) are dissolved in q.s. water. The solution is cooled to 10–15° C. →A. Orlistat (2000 g), micro-crystalline cellulose (1560 g) and sodium starch glycolate (120 g) are pre-mixed→B.

Solution A is given to pre-mix B and kneaded. The resulting material is extruded to spaghettis. This extrudate is spheromized at 700 rpm. The obtained cylinder-shaped wet pellets are dried in a fluidized bed dryer and then sieved. The 0.5–1.25 mm size fractions are collected as orlistat pellets in closed containers.

2. Emulsifier part.

| | |
|---|---|
| Ryoto sugar ester S-170 | 600 mg |
| Microcrystaline cellulose | 312 mg |
| Sodium starch glycolate | 15 mg |
| Povidone | 15 mg |
| Talc | 18 mg |
| Total | 960 mg |

For a batch size of 16 kg pellets the following procedure is applied:

Sugar ester (10 kg) is liquefied by heating to 60° C. Microcrystalline cellulose (5.2 kg), sodium starch glycolate (0.4 kg) and povidone (0.4 kg) are added. The mass is kneaded under cooling to room temperature, then extruded through an extrusion plate with nominal mesh size of 0.7 mm. The fatty extrudate is cut into pieces of 1 mm length and the resulting mass is dusted with talc in a mixer.

Orlistat pellets (2.4 kg) and emulsifier pellets (9.6 kg) are mixed. The mixture is filled into sachets at a fill weight of 1.2 g, corresponding to 120 mg of orlistat and 600 mg of sugar ester.

What is claimed is:

1. A pharmaceutical composition in unit dosage form, said composition comprising an inhibitor of gastrointestinal lipase and at least one additive selected from the group consisting of substantially non-digestible, substantially non-fermentable, hydrophilic and hydrocolloidal food grade thickeners, emulsifiers and mixtures thereof, wherein said composition contains 1 to 300 parts by weight of the thickener, emulsifier or mixtures thereof per 1 part by weight of an inhibitor of gastrointestinal lipase.

2. The composition according to claim 1, wherein the additive is a thickener.

3. The composition according to claim 2, wherein the thickener is a water soluble polysaccharide.

4. The composition according to claim 3, wherein the water soluble polysaccharide is selected from the group consisting of methylcellulose, xanthan gum, psyllium seed, ispaghula husk, plantago ovata seeds, karaya gum, and mixtures thereof.

5. The composition according to claim 1, wherein the additive is an emulsifier.

6. The composition according to claim 5, wherein the emulsifier is a saccharose polyester.

7. The composition according to claim 2 comprising 3 to 30 parts by weight of a thickener per 1 part by weight of an inhibitor of gastrointestinal lipase.

8. The composition according to claim 5 comprising 3 to 30 parts by weight of an emulsifier per 1 part by weight of an inhibitor of gastrointestinal lipase.

9. The composition according to claim 1, wherein the inhibitor of gastrointestinal lipase is orlistat.

10. The composition according to claim 1, wherein said unit dosage form is a tablet consisting essentially of orlistat as the active ingredient and of karaya gum or xanthan gum as the thickener, wherein the tablet contains from 50 to 150 mg of orlistat and from 3 to 30 parts by weight of karaya gum or xanthan gum per 1 part by weight of orlistat.

11. The composition according claim 10, wherein the tablet contains about 60 mg of orlistat and about 1.5 g of karaya gum or xanthan gum.

12. The composition according to claim 1, wherein the unit dosage form is selected from the group consisting of tablets, capsules, lozenges, liquid formulations, wafers, crackers and biscuits.

13. A method of reducing anal leakage of oil in a patient to whom orlistat is being administered, which comprises orally administering to the patient 1 to 3 tablets per meal consumed by the patient, each of the tablets containing (i) 50 mg to 150 mg of orlistat and (ii) at least one additive selected from the group consisting of karaya gum and xanthan gum, the karaya gum or xanthan gum being present in the amount of 3 parts to 30 parts by weight of karaya gum or xanthan gum per 1 part by weight of orlistat.

14. The method according to claim 13, wherein the tablet contains about 100 mg of orlistat and of about 2 g of karaya gum or xanthan gum.

\* \* \* \* \*